(12) United States Patent
Malmgren et al.

(10) Patent No.: US 6,657,101 B1
(45) Date of Patent: Dec. 2, 2003

(54) ABSORBENT STRUCTURE IN AN ABSORBENT ARTICLE

(75) Inventors: Kent Malmgren, Harmonigatan (SE); Shabira Abbas, Kåserigatan (SE); Bengt Widberg, Begevägen (SE); Åsa Östman, Spaldingsgatan (SE); Jeanette Annergren, Bäckvägen (SE); Camilla Bemm, Karlegatan (SE); Eva Strömbom, Gundas Gata (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/651,129

(22) Filed: Aug. 30, 2000

(30) Foreign Application Priority Data

Aug. 30, 1999 (SE) ................................. 9903073

(51) Int. Cl.[7] ................................. A61F 13/15
(52) U.S. Cl. ................... 604/367; 604/369; 604/375; 604/377
(58) Field of Search .................. 604/367, 369, 604/376, 375, 377, 384; 428/304.4, 318.4, 320.2

(56) References Cited

U.S. PATENT DOCUMENTS

| | | | |
|---|---|---|---|
| 3,122,140 A | * 2/1964 | Crowe, Jr. ................... | 604/369 |
| 3,301,257 A | * 1/1967 | Crowe, Jr. et al. .......... | 604/366 |
| 3,545,441 A | * 12/1970 | Gravdahl ..................... | 128/284 |
| 3,598,742 A | 8/1971 | Jamison et al. | |
| 4,104,435 A | * 8/1978 | Ballesteros ................. | 428/288 |
| 4,239,043 A | * 12/1980 | Gellert ........................ | 128/285 |
| 4,394,930 A | 7/1983 | Korpman | |
| 4,902,565 A | * 2/1990 | Brook ...................... | 428/315.5 |
| 4,985,467 A | * 1/1991 | Kelly et al. .................... | 521/52 |
| 5,147,345 A | * 9/1992 | Young et al. ................ | 604/378 |
| 5,338,766 A | * 8/1994 | Phan et al. .................... | 521/63 |
| 5,713,881 A | * 2/1998 | Rezai et al. ................. | 604/368 |
| 5,795,921 A | * 8/1998 | Dyer et al. .................. | 521/146 |
| 6,103,358 A | * 8/2000 | Bruggemann et al. ... | 428/317.9 |
| 6,136,873 A | 10/2000 | Hahnle et al. | |

FOREIGN PATENT DOCUMENTS

| | | |
|---|---|---|
| DE | 195 40 951 A1 | 5/1997 |
| EP | 0 044 624 | 10/1984 |
| EP | 0 598 833 | 6/1994 |
| SE | 9801694-2 | 11/1999 |
| WO | 93/04092 | 3/1993 |
| WO | 94/22502 | 10/1994 |
| WO | 96/16624 | 6/1996 |

* cited by examiner

Primary Examiner—Weilun Lo
Assistant Examiner—Jacqueline Stephens
(74) Attorney, Agent, or Firm—Burns, Doane, Swecker & Mathis, L.L.P.

(57) ABSTRACT

The invention refers to an absorbent structure in an absorbent article such as a diaper, a pant diaper, an incontinence guard, a sanitary napkin etc., the absorbent structure comprises an open-cell foam structure, the pore walls of said foam structure comprising a liquid-storing material having the capacity to store more than 7% synthetic urine defined according to the CRC method. The absorbent structure is characterized by that the pores of the foam structure contains hydrophilic fibers, at which at least the main part of the hydrophilic fibers are firmly anchored in the pore walls of the foam structure, and that the fiber amount is at least 10% by weight of the total weight of the open-cell foam in dry condition. The invention also refers to an absorbent article containing such an absorbent structure.

24 Claims, 7 Drawing Sheets

| Material | Volume (cm$^3$/g) | Distribution length (cm) |
|---|---|---|
| Sample 5 | 15,3 | 12,25 |
| Sample 6 | 5,4 | 16,5 |
| Sample 3 | 1,5 | 20,25 |

FIG.4

| Material | Storage capacity (%) |
|---|---|
| Sample 7 | 18 |
| Sample 8 | 15 |
| Sample 9 | 12 |
| Sample 10 | 7 |
| Sample 4 | 5,5 |

FIG.5

ABSORBENT STRUCTURE IN AN ABSORBENT ARTICLE

TECHNICAL FIELD

The present invention refers to an absorbent structure in an absorbent article such as a diaper, a pant diaper, an incontinence guard, a sanitary napkin etc. said absorbent structure comprises an open-cell foam structure, the pore walls of said foam structure comprising a liquid-storing material having the capacity to store more than 7% synthetic urine defined according to the CRC method.

BACKGROUND

Absorbent articles of the above mentioned kind are intended to absorb body liquids such as urine and blood. Such absorbent articles usually have a liquid pervious topsheet, which during use is facing the wearer's body. They further have a liquid impervious backsheet, e g a plastic film, a plastic coated nonwoven or a hydrophobic nonwoven, and an absorbent structure enclosed between the liquid pervious topsheet and the liquid impervious backsheet.

It is desired that absorbent articles of the above mentioned kind are thin an discrete to use. It is further important that absorbent articles of the above mentioned kind have a high liquid acquisition capacity as well as liquid distributing and liquid storing capacity. In order to fulfil these requirements it is common that the absorbent structure contains two or more layers having different properties.

In order to obtain a good liquid acquisition capacity it is important that the liquid acquisition layer has a high morentaneous liquid acquisition capacity. Open, bulky structures with large capillaries have a high momentaneous liquid acquisition capacity and examples of such material are cellulosic fluff pulp of thermomechanic or chemithermomechanic (CTMP) type, chemically stiffened cellulosic fibers, synthetic fiber structures of different kind and porous foam materials.

In order to obtain a good liquid storing capacity it is common that the absorbent structure comprises one or more layers which contain superabsorbent materials. Superabsorbent materials are crosslinked polymers with the capacity to absorb liquid many times their own weight. A commonly occurring superabsorbent material is crosslinked polyacrylate. The absorption mechanism of such superabsorbents is based on the fact that the polymer chain contains a plurality of anionic carboxy groups, which make it possible for the polymer to by means of osmotic forces absorb aqueous liquids. The superabsorbent material is often in the form of small particles, which are arranged and contained in a fibrous matrix. The fibrous matrix usually consists of cellulosic fluff pulp of thermomechanic, chemical or chemithermomechanic type, but a certain amount of synthetic fibers is also commonly occurring, One problem with absorbent structures containing superabsorbent material, is that it is difficult to distribute and maintain the superabsorbent material in the desired location in the absorbent structure, both during storage and during use of the article. Another problem with absorbent structures containing superabsorbent material, is so called gel blocking. This problem occurs by the fact that the liquid-containing superabsorbent particles swell and form a gel. The gel blocks the liquid transport and gives rise to an accumulation of liquid in certain portions of the absorbent structure while other portions of the structure becomes more or less non-utilized.

One problem occuring in absorbent structure containing several layers, is that the uniting capacity of the absorbent core during use can be insufficient. This can involve that the structure breaks or crumbles. A further problem with absorbent structures containing several different layers is that it can be difficult to achieve a good liquid transport between the different layers. The joining is also costly and material- and energy demanding.

Another known liquid-absorbing structure is polymeric foams with open cells. Polymeric foams with superabsorbent properties for use in absorbent articles are disclosed in for example EP 0,044,624 and in U.S. Pat. No. 4,394,930. One problem with polymeric foams having superabsorbent properties is however that they are relatively weak, i e such foam materials tend to break when mechanically loaded.

In EP 0,598,833 there is disclosed a foam material for use as an absorbent structure in for example diapers. The foam material has a specified pore volume, specific surface area and ability to recover its volume after compression. The foam consists of a so called "HIPE"-foam (high internal phase emulsion), which means that the foam is produced by polymerization of a water-in-oil emulsion.

In U.S. Pat. No. 3,598,742 there is disclosed an open-cell foam which for increasing the strength of the foam contains between 30 and 90 weight percent fibers, based on the dry weight of the foam. The structure is manufactured by mixing fibers, surfactant, water and a thickener with a dispersion containing a film-forming water insoluble substance. The water insoluble substance is for example polyvinyl acetate and copolymers thereof.

There is further in SE9801694-2 disclosed an absorbent structure comprising a carrier material in the form of an open-cell foam, at which the foam in its pore structure contains hydrophilic fibers. The function of the carrier material is to create a structure having high resilient recovery both in dry and wet condition.

DESCRIPTION OF THE INVENTION

The problem of providing an integrated absorbent structure for use in an absorbent article having a sufficient high liquid distributing as well as liquid acquisition capacity, has been substantially eliminated by the present invention.

An absorbent porous structure according to the invention comprises a polymeric open-cell foam structure, in which the pore walls of the foam structure comprises a liquid-storing material, at which the liquid-storing material in the pore walls of the foam structure has the ability to store more than 7% synthetic urine, defined according to the CRC method. The absorbent structure is mainly characterized by that the pores of the foam structure contains hydrophilic fibers, at which at least the main part of the hydrophilic fibers are firmly anchored in the pore walls of the foam structure, and that the fiber amount is at least 10% by weight of the total weight of the open-cell foam in dry condition.

The definition "liquid-storing material" according to the invention refers to a material which has the capacity to store more than 7% synthetic urine, defined according to the CRC method. The liquid-storing capacity is measured by letting the material absorb liquid freely until saturated at which weight$_{(saturation)}$ is obtained. After that the sample is centrifugated during 10 minutes at 1500 rpm, which approximately corresponds to a load of 300 g. The sample is weighed after centrifugation, at which weight$_{(centrifugation)}$ is obtained. By then calculating the quotient between weight$_{(centrifugation)}$ and weight$_{(saturation)}$ and multiply with 100 the storage capacity of the sample in percent is obtained.

The advantage of the absorbent structure according to the invention is that it has good liquid storage capacity and good liquid distribution. By the fact that the foam contains a relatively high amount of fibers the mechanical properties of the foam are further improved, which involves that the structure withstands higher mechanical stresses than a foam of a superabsorbent material without fibers or alternatively with a small amount of fibers. The ability of the foam to withstand both tensile and shearing stresses is improved. Further the foam is more easily compressed, i e it can be compressed to higher densities and yet expand when whetted. The latter improves the capacity of the foam to by capillary action absorb liquid after compression and since often thinness of absorbent articles are strived at, fiber addition may give certain advantages. Fiber addition further improves the liquid distributing capacity of the foam. Another advantage associated with an absorbent foam structure according to the invention, is that it is more flexible and pliable than a structure that is mainly based on fibers. By the fact that the superabsorbent material is in the form of a foam structure, the problem of high amounts of dusts associated with the manufacture of absorbent structures containing superabsorbent materials in the form of small particles, is avoided.

Examples of hydrophilic fibers are different types of hydrophilic natural or synthetic fibers. Some examples of fibers are pulp fibers of CTMP (chemithermomechanical pulp), HT CTMP (high temperature chermithermomechanical pulp), CP (chemical pulp) and fibrous CMC (carboxy methyl cellulose). Other useful hydrophilic fibers are for example cotton fibers, viscous fibers and fibers of superabsorbent material such as for example polyacrylate. It is further possible to use crosslinked cellulose fibers, so called "curly fibers". For controlling the properties of the produced foam such as stiffness and liquid distribution, it is also possible to vary the length and coarseness of the fibers.

According to a preferred embodiment the hydrophilic fibers amount to 20–80 weight percent of the total weight of the polymeric open-cell foam in dry condition. Such a structure has a better liquid distributing capacity than structures having a lower amount of hydrophilic fibers. When the absorbent structure contains more than 80 weight percent fibers, based on the total weight of the structure in dry condition, the absorbent structure loses its softness and flexibility and can be felt as being stiff and uncomfortable when being used in an article. According to a more preferred embodiment the fibers amount to 20–60 weight percent of the total weight of the polymeric open-cell foam in dry condition.

According to one embodiment the structure comprises as seen in the z-direction a liquid acquisition portion, at which the liquid acquisition portion contains a higher amount of hydrophilic fibers than the liquid storage portion. One advantage of such a structure is that the upper part of the absorbent structure located closest to the wearer, gets a higher liquid distributing capacity than the lower liquid storage portion of the absorbent structure. In order to obtain such a fiber gradient different layers are manufactured and placed on top of each other. By applying the different layers on top of each other before they are dry an integrated structure will be obtained, where the layers partly penetrate into each other. One advantage of such an integrated structure as compared to an absorbent structure consisting of separate layers is that a subsequent joining step is eliminated. Such a structure is thus cheaper to manufacture since the need for an adhesive and/or energy supply for joining the layers is eliminated. Another advantage with an integrated structure is that the function of the structure is improved in such a way that the liquid transport does not risk to be deteriorated at the transition from a first layer to a second layer due to insufficient contact between the layers.

According to an embodiment the pore walls of the foam structure in the liquid acquisition portion is more crosslinked than the pore walls of the liquid storage portion. A very highly crosslinked superabsorbent material can not receive so much liquid as a superabsorbent material having a lower degree of crosslinking. A superabsorbent material with a high degree of crosslinking has lower risk for gelblocking. An absorbent structure according to this embodiment is made by preparing two or more foam layers, at which a higher amount of crosslinking agent is added to the polymer solution which is going to form the liquid acquisition layer and a smaller amount of crosslinking agent is added to the polymers solution that is going to form liquid storage portion. After foaming and crosslinking but before drying the different layers are placed on top of each other, at which the layers will partly integrate with each other and a continuous structure is achieved.

By making a foam with different portions according to above is is possible to control the absorption properties so that an integrated structure is obtained which has a rapid liquid acquisition, good liquid distribution as well as storage capacity.

The foam has both in uncompressed dry condition, in compressed dry condition and after swelling in synthetic urine a mean pore size below 1000 micrometer, and preferably below 500 micrometer.

According to an embodiment the liquid storage material in the foam structure is a polysaccharide. Examples thereof are carboxy methyl cellulose, other cellulose derivatives, starch, starch derivatives, chitosan, alginate and pectin. Such a foam can be made by dissolving a polymer in a solvent. To the solution there are added hydrophilic fibers and a surfactant, after which foaming is produced for example by vigorous mechanical agitation. The foamed mixture is crosslinked with a crosslinking agent, after which the temperature of the formed foam is lowered to a temperature below the freezing point of the solvent and continuing the crosslinking reaction during the freezing step. Then the main part of the solvent is removed from the formed foam material. Two or more different surfactants may further be added in order to control the properties, such as porosity and stability, of the produced foam.

According to another embodiment the liquid storage portion is based on polyacrylate. Such a foam can for example be made by adding acrylic acid, water, sodium hydroxide, surfactant, hydrophilic fibers (for example cellulose fibers) and crosslinking agent to a beaker. This solution is then foamed mechanically with an electric beater for up to half an hour. Then an initiator is added and the solution is exerted to further mechanical working for some minutes. Finally the foamed solution is transferred to a mould and polymerization is initiated by supply of heat which results in a solid foam material. Manufacture of polyacrylate foams without content of fibers is described in detail in DE 19540951 A1.

The invention of course also comprises foams of other materials having a high liquid storage capacity, and foams made in other ways as described above.

The invention also refers to an absorbent article such as incontinence guard diaper, pant diaper, sanitary napkin and the like and of the kind comprising a liquid pervious topsheet, a liquid impervious backsheet and an absorbent structure applied therebetween, said absorbent structure containing a structure according to any of the embodiments described above.

The absorbent structure according to the invention is in the absorbent article preferably arranged over the entire absorption body of the absorbent article, and is preferably the sole layer in the absorption body and thus has a high liquid acquisition, good liquid distribution and good liquid storage capacity. It is however also possible that the absorbent foam structure according to the invention only makes a part of the total surface of the absorption body of the absorbent article, e g at the intended wetting area where the discharged body liquid will be received and which normally is displaced towards the front of the article. The portions of the absorption body located outside the intended wetting area may then be of an optional other absorbent material. It is also possible that the liquid acquisition portion is only applied over the area which is intended as wetting area, while the liquid storage portion is arranged over the entire surface of the absorbent structure. Such an embodiment is especially preferred when used as an absorbent structure in a sanitary napkin. The liquid acquisition portion swells in z-direction upon absorption of body liquid and forms a hump.

SHORT DESCRIPTION OF THE DRAWINGS

FIG. 4 shows a table over the liquid distribution length for samples having different bulk.

FIG. 5 shows a table over the storage capacity at different period of times for samples having different fiber contents.

EMBODIMENTS

Below measurements of the liquid distribution, liquid storage and liquid absorption capacities will be disclosed.

Measurement of the Liquid Distribution Capacity

Figure 1:
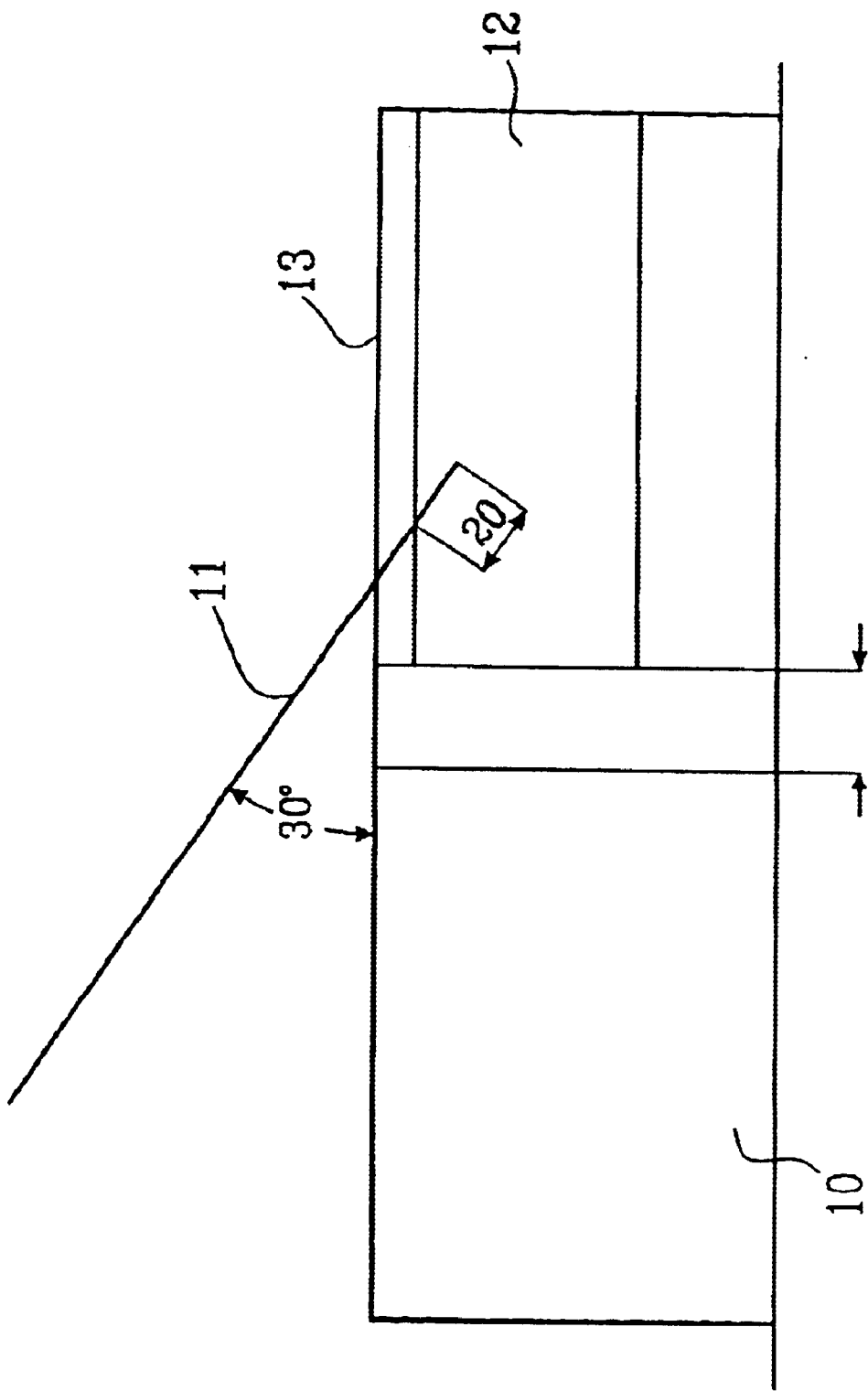
FIG. 1 shows a measuring apparatus for measuring the liquid distribution capacity.

In this method it is measured how long distance of the sample is wet after one end portion of the sample has been in contact with a liquid container with synthetic urine for 30 seconds, 1, 2, 3, 4, 5, 10, 20, 30, 40, 50 and 60 minutes. Besides it is measured how large amount of liquid has been absorbed during the same time. The sample is placed on a plexi glass plate having an inclination of 30 degrees with respect to the horizontal plane. A measuring apparatus which is schematically shown in FIG. 1 was used at the test. The measuring apparatus comprises a scale 10, a plexi glass plate 11 and a liquid container 12, in which the liquid surface is indicated with 13. The liquid container 12 is placed adjacent the scale 10, at which it is important that both take a horizontal position. The plexi glass plate 11 is placed on the scale with an inclination of 30 degrees with respect to the horizontal plane without touching the liquid container 12. Test liquid is poured into the liquid container 12 so that 2 cm of the plexi glass plate is below the liquid surface 13. The sample is weighed with an accuracy of measurement of 0,1 g and is placed on the plexi glass plate 11 without the sample touching the liquid. The width of the sample is 2 cm and its length is 28 cm. The scale is then tarred and the sample displaced along the plexi glass plate 11 so that the end of the sample is just below the liquid surface 13 and is fixed in this position with a clamp. After exactly 60 minutes the measurement was stopped and the final weight of the sample was noted. It is besides measured how long distance of the sample that is wet, on the underside as well as on the upper side. The mean value of the distribution length on the underside and on the upper side of the sample is stated as the distribution length. The absorption capacity is stated as: $m_2/m_1$ (g/g) where $m_2$ is the weight of the wet sample after the measurement and $m_1$ is the weight of the dry sample before the measurement.

Measurement of the Liquid Storage Capacity

The liquid storage capacity of the samples were measured with the method CRC (centrifuge retention capacity). The sample is firstly allowed to absorb liquid freely until saturation at which $weight_{(saturation)}$ is obtained the sample is centrifugated for 10 minutes at 1500 rpm which approximately corresponds to a load of 300 g. The sample is weighed after the centrifugation, at which $weight_{(centrifugation)}$ is obtained. By calculating the quotient between $weight_{(centrifugation)}$ and $weight_{(saturation)}$ and multiply with 100 the storage capacity of the sample is obtained in percent.

Samples

Sample 1 Carboxy methyl cellulose foam without fibers. The bulk of the foam is 1,2 cm$^3$/g.

Sample 2 Carboxy methyl cellulose foam containing 10 weight percent cellulose fibers of chemical pulp based on the total weight of the sample in dry condition. The bulk of the foam is 1,3 cm$^3$/g.

Sample 3 Carboxy methyl cellulose foam containing 50 weight percent cellulose fibers of chemical pulp based on the total weight of the sample in dry condition. The bulk of the foam is 1,5 cm$^3$/g.

Sample 4 Commercially available viscous foam (Vileda) manufactured by Freudenberg Household Products AB.

Sample 5 Carboxy methyl cellulose foam containing 50 weight percent cellulose fibers of chemical pulp based on the total weight of the sample in dry condition. The bulk of the foam is 15,3 cm$^3$/g.

Sample 6 Carboxy methyl cellulose foam containing 50 weight percent cellulose fibers of chemical pulp based on the total weight of the sample in dry condition. The bulk of the foam is 5,4 cm$^3$/g.

Sample 7 Carboxy methyl cellulose foam without fibers.

Sample 8 Carboxy methyl cellulose foam containing 10 weight percent cellulose fibers of chemical pulp based on the total weight of the sample in dry condition.

Sample 9 Carboxy methyl cellulose foam containing 30 weight percent cellulose fibers of chemical pulp based on the total weight of the sample in dry condition.

Sample 10 Carboxy methyl cellulose foam containing 50 weight percent cellulose fibers of chemical pulp based on the total weight of the sample in dry condition.

Preparation of Samples

Sample 1 and 7 were prepared as follows:

Two liquid foams were prepared by vigorous mixing of the following mixtures:

10 g of a 3% solution of Celpol RX in water, 40 g water, 0,057 g NaOH, 0,5 g Berocell 451 and 0,5 g Berol 048.

110 g of a 3% solution of Cekol 50000 in water, 40 g water, 0,091 g NaOH, 0,5 g Berocell 451 and 0,5 g Berol 048.

The two foams were cooled to a temperature of 2° C. after which 0,264 g cyanuric chloride dissolved in 10 g methyl ethyl ketone was added to said first foam. After vigorous stirring for about 3 minutes the foams were mixed carefully for about 2 minutes. After that the foam was spread out to a layer having an area of about 1600 cm$^2$ on a plane plastic surface (PVC) and was frozen at about −18° C. After about 20 hours the frozen foam was released from the plastic surface and was thawed in a water bath. A water swollen but insoluble foam was achieved. It was washed an deswollen by leaching in ethanol and dried at room temperature.

Samples 2, 3, 5, 6, 8, 9 and 10 were prepared in the same way as sample 1 and 7 but with the difference that bleached sulphate was added to the polymer solution before foaming.

Samples 3 and 6 are the same starting material as sample 5, but with the difference that samples 3 and 6 had been calendered (i e passed between two hot rolls) 2 and 4 times respectively. Sample 5 had not been calendared. This involves that these samples have different bulks.

Test Liguid

As test liquid was used synthetic urine according to the following recipe: 0,66 g/l MgSO$_4$, 4,47 g/l KCl, 7,60 g/l NaCl, 18,00 g/l NH$_2$CONH$_2$ (urea), 3,54 g/l KH$_2$PO$_4$, 0,745 g/l Na$_2$HPO$_4$, 1 ml/l of a 0,1% solution of Triton X-100, which is a surfactant sold by Aldrich. The substances were dissolved in deionized water.

Results

Figure 2:
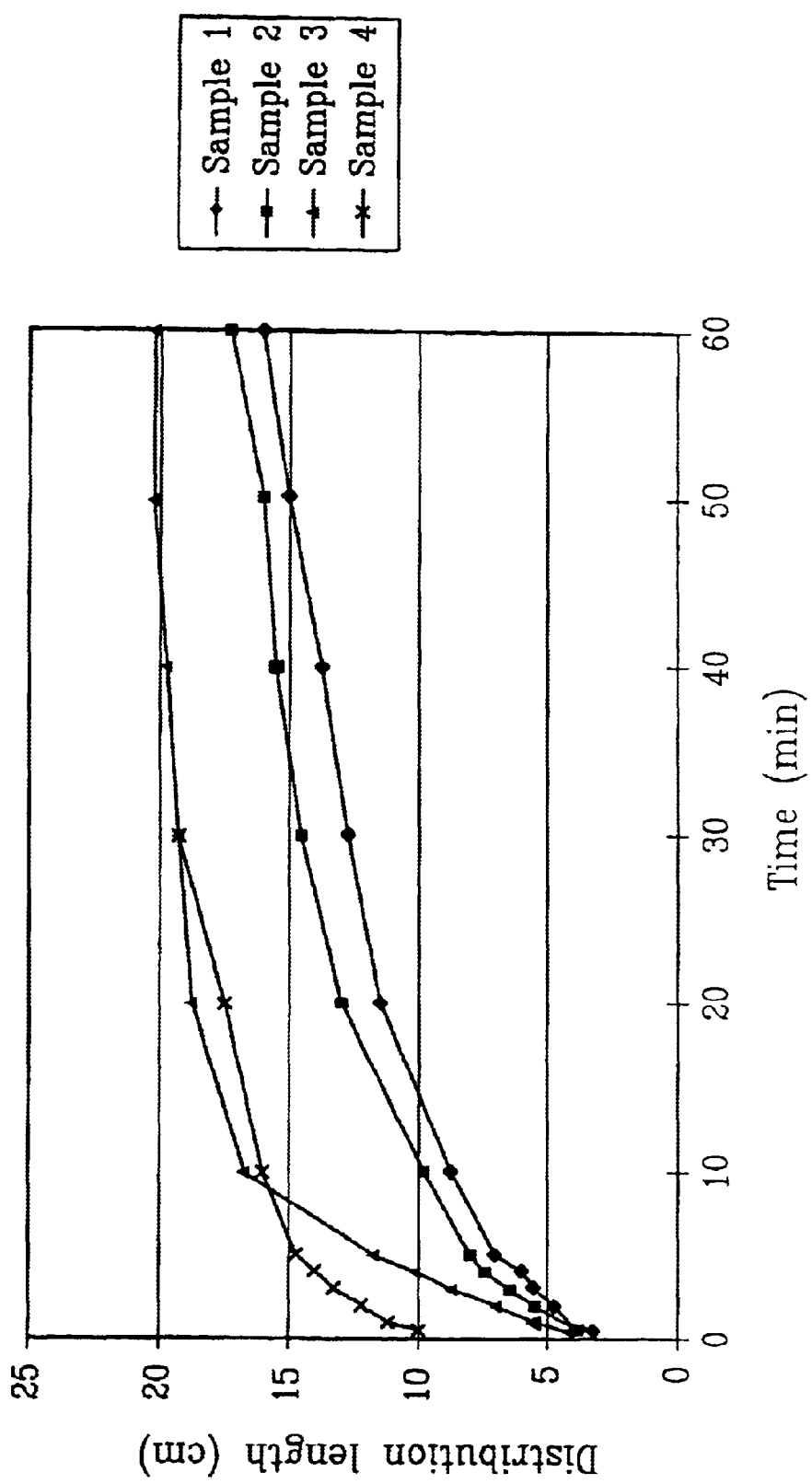
FIG. 2 shows a diagram over the liquid distribution length at different period of times for samples having different fiber contents.

In FIG. 2 there is disclosed a diagram over the liquid distribution length for samples 1,2,3 and 4 at different periods of time.

Figure 3:
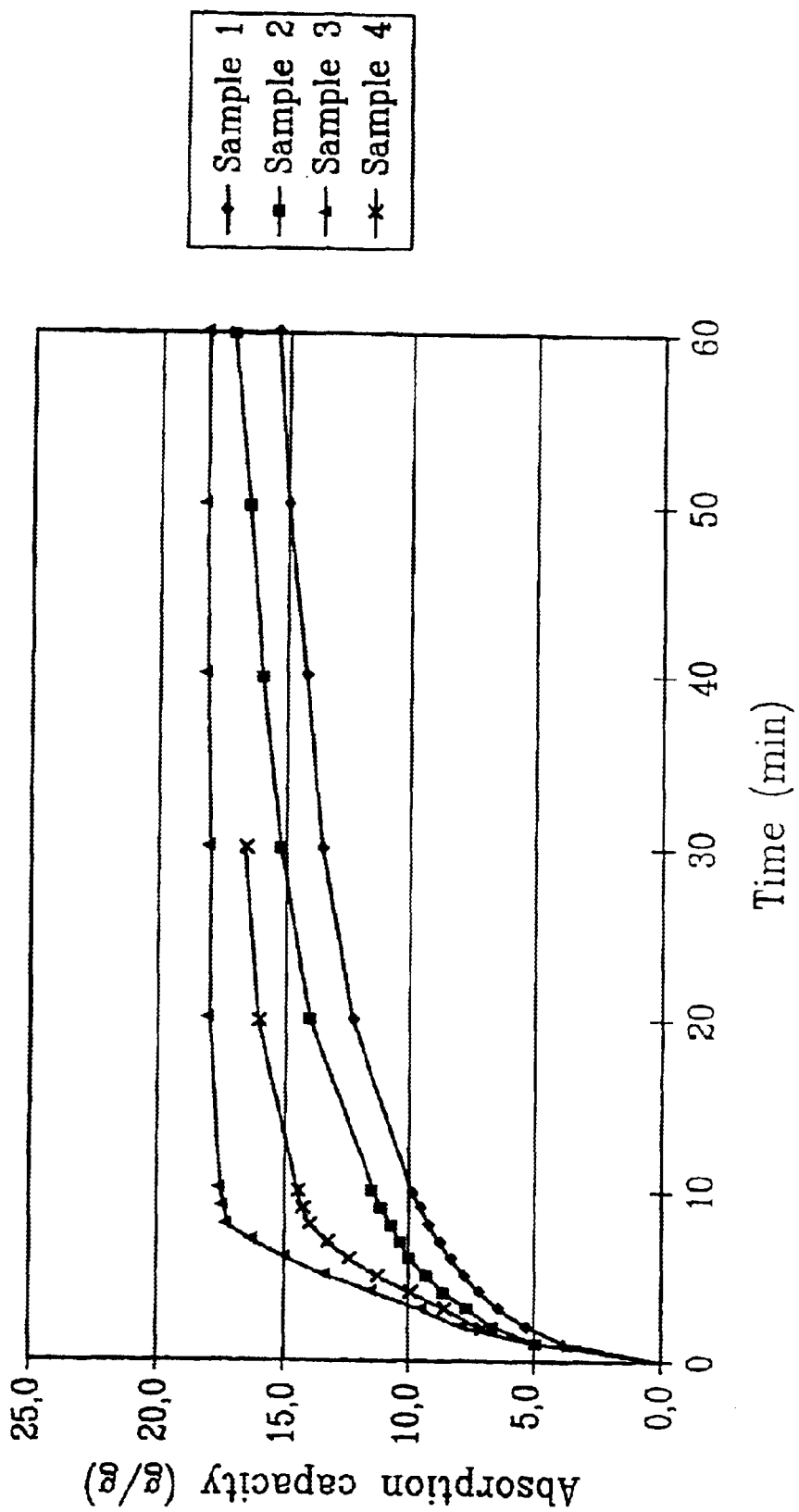
FIG. 3 shows a diagram over the absorption capacity at different period of times for samples having different fiber contents.
Figure 6:
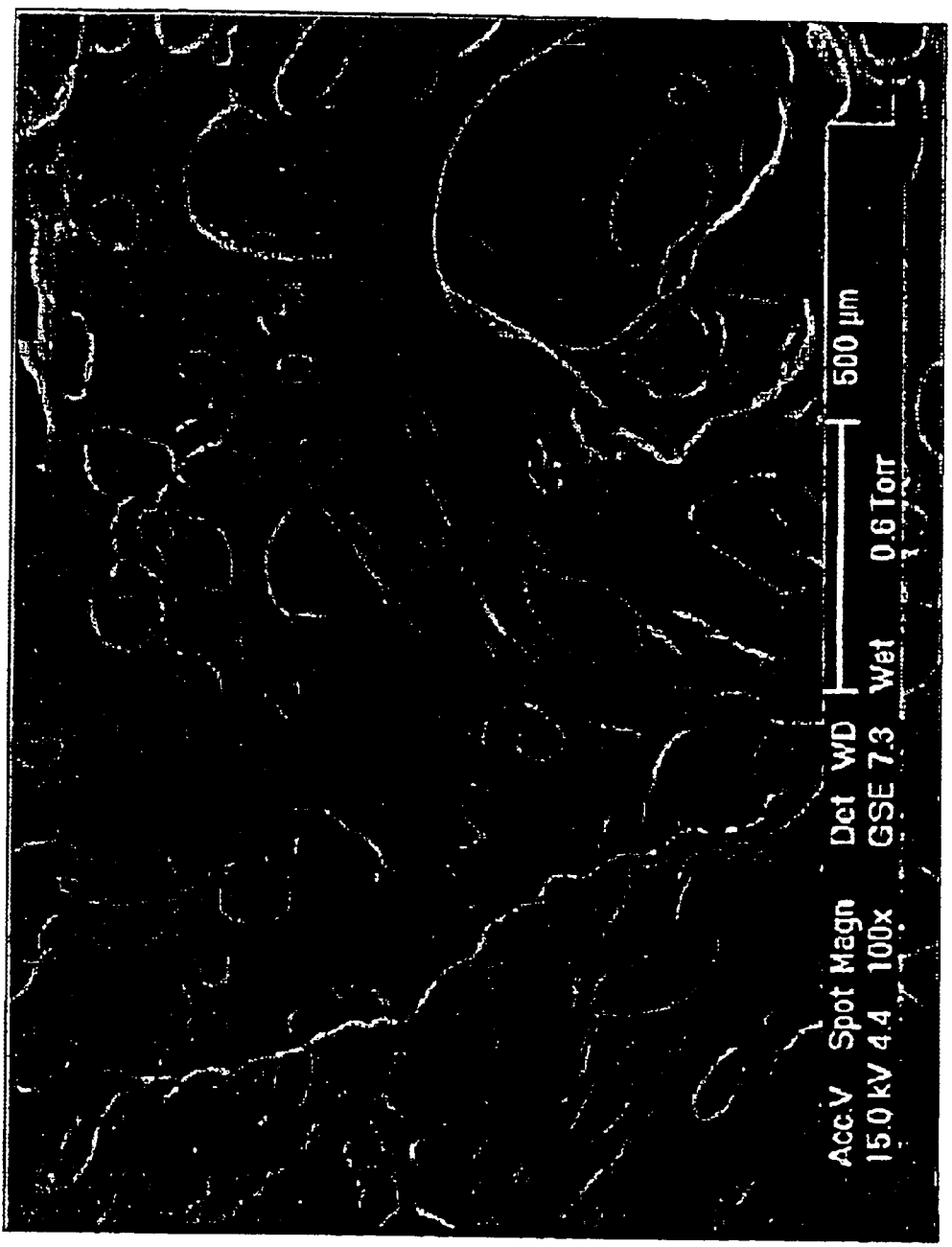
FIG. 6 shows an electron microscope picture (ESEM) of a polyacrylate foam without fibers.
Figure 7:
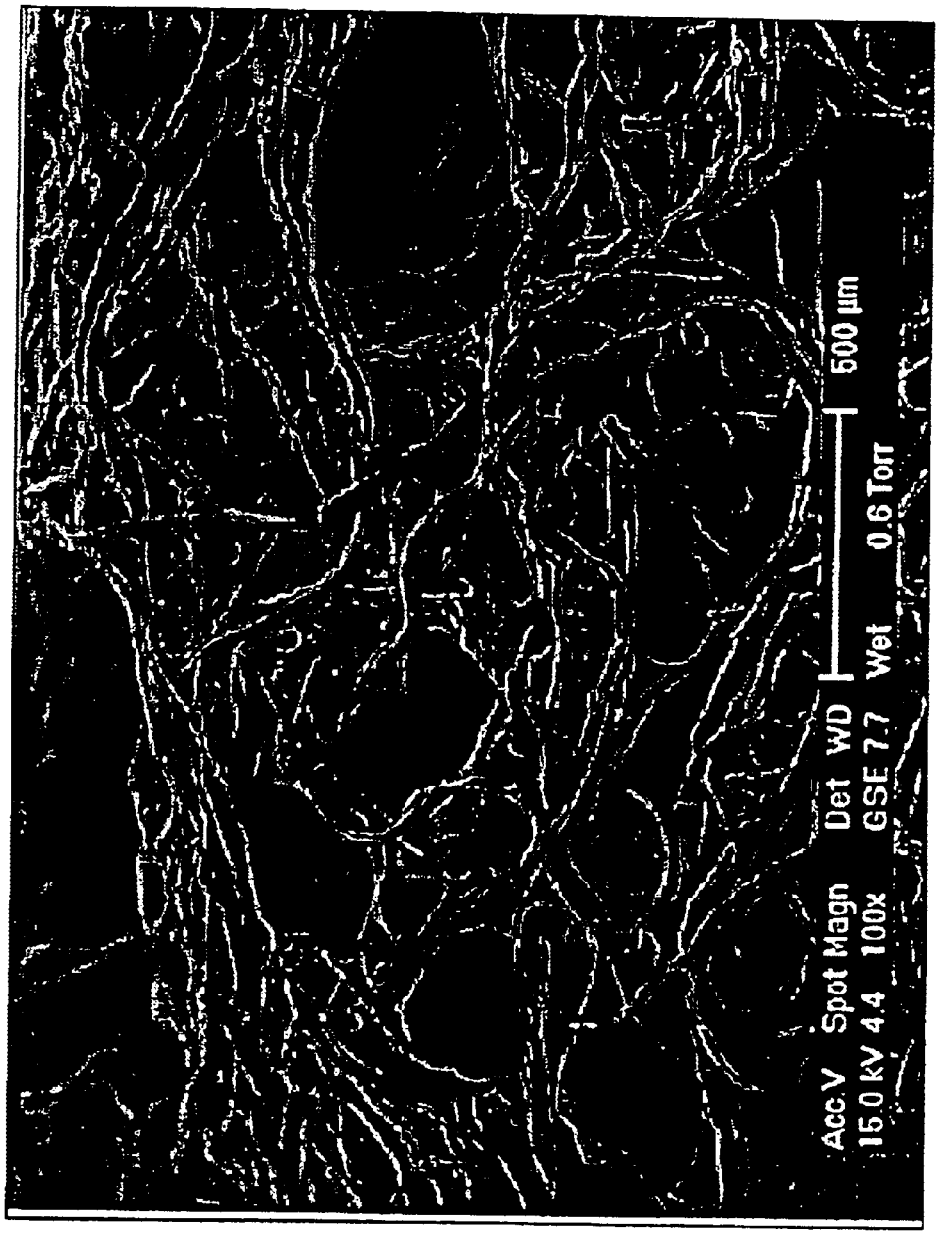
FIG. 7 shows an electron microscope picture (ESEM) of a polyacrylate foam containing 10 weight percent chemical pulp.
Figure 8:
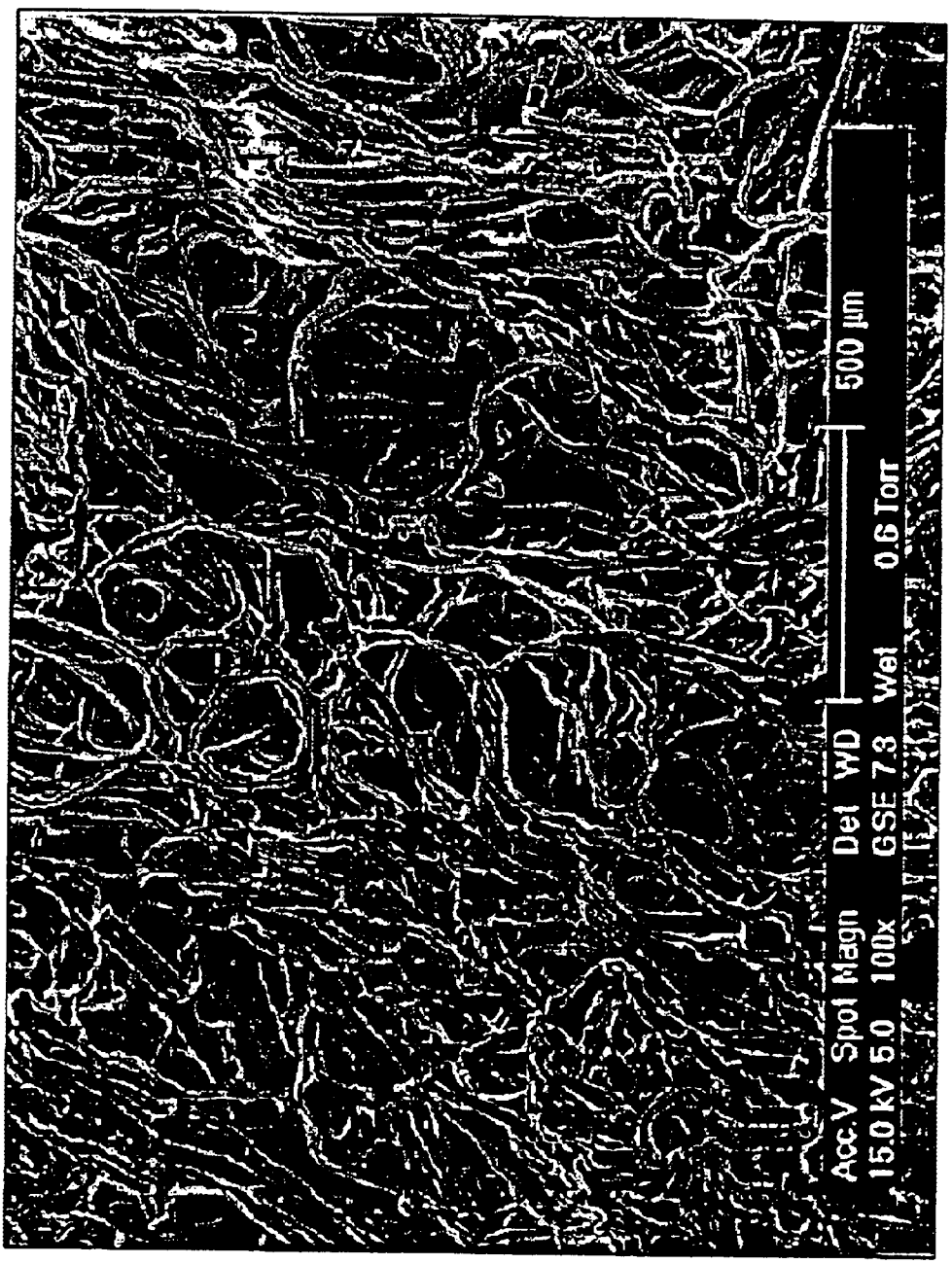
FIG. 8 shows an electron microscope picture (ESEM) of a polyacrylate foam containing 25 weight percent chemical pulp.

In FIG. 3 there is shown the absorption capacity for samples 1,2,3 and 4 at different periods of time.

In FIG. 4 there is shown the liquid distribution length for 3,5 and 6 at different periods of time.

In FIG. 5 there is shown the storage capacity for samples 7,8,9,10 and 4.

The invention is of course not limited to the above disclosed embodiments, but may be applied for other embodiments within the scope of the claims.

What is claimed is:

1. An absorbent structure in an absorbent article, said absorbent structure comprising:

an open-cell foam having pore walls, said pore walls of said open-cell foam comprising a liquid-storing material having a capacity to store more than 7% synthetic urine defined according to a CRC method, wherein pores of the open-cell foam contain hydrophilic fibers, at which at least a main part of the hydrophilic fibers are firmly anchored in the pore walls of the open-cell foam, and that a hydrophilic fiber amount is at least 10% by weight of a total weight of the open-cell foam in dry condition.

2. An absorbent structure as claimed in claim 1 wherein the hydrophilic fiber amount is 20–80% by weight of the total weight of the open-cell foam in dry condition.

3. The absorbent structure of claim 2 wherein the open cell foam is made from one of cellulose, starch, and polyacrylate.

4. The absorbent structure of claim 2 wherein the open cell foam has pores having a mean diameter of less than 1000 micrometers.

5. The absorbent structure of claim 2 further comprising a top surface and a bottom surface wherein the top surface is covered with a liquid pervious layer and the bottom surface is covered with a liquid impervious layer.

6. An absorbent structure as claimed in claim 1 wherein the hydrophilic fiber amount is 20–60% by weight of the total weight of the open-cell foam in dry condition.

7. The absorbent structure of claim 6 wherein the open cell foam is made from one of cellulose, starch, and polyacrylate.

8. The absorbent structure of claim 6 wherein the open cell foam has pores having a mean diameter of less than 1000 micrometers.

9. The absorbent structure of claim 6 further comprising a top surface and a bottom surface wherein the top surface is covered with a liquid pervious layer and the bottom surface is covered with a liquid impervious layer.

10. An absorbent structure as claimed in claim 1 wherein the open-cell foam forms a liquid acquisition portion at a surface of the absorbent structure and a liquid storage portion underlying the liquid acquisition portion, wherein the liquid acquisition portion contains a higher amount of hydrophilic fibers than the liquid storage portion.

11. The absorbent structure of claim 10 wherein the open cell foam is made from one of cellulose, starch, and polyacrylate.

12. The absorbent structure of claim 10 wherein the open cell foam has pores having a mean diameter of less than 1000 micrometers.

13. The absorbent structure of claim 10 further comprising a top surface and a bottom surface wherein the top surface is covered with a liquid pervious layer and the bottom surface is covered with a liquid impervious layer.

14. An absorbent structure as claimed in claim 1 wherein the open-cell foam is a crosslinked polymer, wherein the pore walls in a liquid acquisition portion are more crosslinked than the pore walls of a liquid storage portion of the open-cell foam.

15. The absorbent structure of claim 14 wherein the open cell foam is made from one of cellulose, starch, and polyacrylate.

16. The absorbent structure of claim 14 wherein the open cell foam has pores having a mean diameter of less than 1000 micrometers.

17. The absorbent structure of claim 14 further comprising a top surface and a bottom surface wherein the top surface is covered with a liquid pervious layer and the bottom surface is covered with a liquid impervious layer.

18. An absorbent structure as claimed in claim 1 wherein the open cell foam is based on one of cellulose and starch.

19. An absorbent structure as claimed in claim 1 wherein a liquid storage portion is based on polyacrylate.

20. An absorbent structure as claimed in claim 1 wherein a diameter of a mean pore size in the open-cell foam is below 1000 micrometers.

21. An absorbent article comprising a liquid pervious topsheet, a liquid impervious backsheet and an absorbent structure as claimed in claim 1 arranged therebetween.

22. The absorbent article of claim 21 wherein the absorbent article is one of a diaper, an incontinence guard, a pant diaper, and a sanitary napkin.

23. The absorbent structure of claim 21 wherein the absorbent article is one of a diaper, an incontinence guard, a pant diaper, and a sanitary napkin.

24. An absorbent structure for an absorbent article, said absorbent structure comprising:
- a liquid acquisition portion including
    - an open-cell foam having pore walls,
        - the pore walls of said open-cell foam comprising a liquid-storing material having a capacity to store more than 7% synthetic urine defined according to a CRC method,
    - wherein pores of the open-cell foam contain hydrophilic fibers anchored in the pore walls of the open-cell foam,
    - the hydrophilic fibers being at least 10% by weight of a total weight of the open-cell foam in dry condition; and
- a liquid distribution or liquid storage layer in contact with and underlying the liquid acquisition portion, the liquid acquisition portion having a greater amount of hydrophilic fibers than the liquid distribution or liquid storage layer.

* * * * *